United States Patent
Nadgoud et al.

(10) Patent No.: US 9,688,682 B2
(45) Date of Patent: Jun. 27, 2017

(54) CRYSTALLINE FORMS OF PEMETREXED TROMETHAMINE SALTS

(71) Applicant: DR. REDDY'S LABORATORIES LIMITED, Hyderabad (IN)

(72) Inventors: Ramesh Kumar Nadgoud, Hyderabad (IN); Sridhar Vasam, Warangal (IN); Siva Reddy Makireddy, Guntur (IN); Goverdhan Gilla, Hyderabad (IN); Syam Kumar Unniaran Kunhimon, Thissur (IN); Sachin Sharma, Kangra (IN); Kumara Swamy Dornala, Nalgonda (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 0 days.

(21) Appl. No.: 14/905,736

(22) PCT Filed: Jul. 15, 2014

(86) PCT No.: PCT/IB2014/063123
§ 371 (c)(1),
(2) Date: Jan. 15, 2016

(87) PCT Pub. No.: WO2015/008221
PCT Pub. Date: Jan. 22, 2015

(65) Prior Publication Data
US 2016/0168153 A1   Jun. 16, 2016

(30) Foreign Application Priority Data
Jul. 16, 2013   (IN) ............................ 3180/CHE/2013

(51) Int. Cl.
| C07D 487/00 | (2006.01) |
| C07D 487/04 | (2006.01) |
| C07C 213/08 | (2006.01) |
| C07C 215/10 | (2006.01) |

(52) U.S. Cl.
CPC .......... *C07D 487/04* (2013.01); *C07C 213/08* (2013.01); *C07C 215/10* (2013.01); *C07B 2200/13* (2013.01)

(58) Field of Classification Search
None
See application file for complete search history.

(56) References Cited

U.S. PATENT DOCUMENTS

| 5,344,932 | A | 9/1994 | Taylor |
| 7,138,521 | B2 | 11/2006 | Chelius et al. |
| 8,324,382 | B2 | 12/2012 | Luo et al. |
| 9,156,841 | B2 | 10/2015 | Busolli et al. |
| 2011/0201631 | A1 | 8/2011 | Kocherlakota et al. |
| 2011/0319354 | A1 | 12/2011 | Layton et al. |
| 2012/0329819 | A1 | 12/2012 | Albrecht et al. |

FOREIGN PATENT DOCUMENTS

| CN | 1552713 A | 12/2004 |
| CN | 1778802 A | 5/2006 |
| CN | 101033227 A | 9/2007 |
| CN | 101691371 B | 1/2012 |
| EP | 0432677 A1 | 6/1991 |
| WO | 01/14379 A2 | 3/2001 |
| WO | 2006/136837 A2 | 12/2006 |
| WO | 2012/015810 A2 | 2/2012 |

OTHER PUBLICATIONS

International Search Report mailed on Nov. 24, 2014, for corresponding International Patent Application No. PCT/IB2014/063123.
Written Opinion mailed on Nov. 24, 2014, for corresponding International Patent Application No. PCT/IB2014/063123.
International Preliminary Report on Patentability issued on Jan. 19, 2016, for corresponding International Patent Application No. PCT/IB2014/063123.

*Primary Examiner* — Jeffrey H Murray
(74) *Attorney, Agent, or Firm* — Pergament & Cepeda LLP; Milagros A. Cepeda; Edward D. Pergament

(57) ABSTRACT

The present invention is directed to novel crystalline forms of pemetrexed tromethamine salts and processes for preparation thereof.

15 Claims, 4 Drawing Sheets

CRYSTALLINE FORMS OF PEMETREXED TROMETHAMINE SALTS

This application is a National Stage Application under 35 U.S.C. §371 of PCT International Application No. PCT/IB2014/063123, filed Jul. 15, 2014, which claims the benefit of Indian Provisional Application No. 3180/CHE/2013, filed Jul. 16, 2013, all of which are hereby incorporated by reference in their entireties.

INTRODUCTION

The present invention is directed to novel crystalline forms of pemetrexed tromethamine salts and processes for preparation thereof.

BACKGROUND OF THE INVENTION

Pemetrexed, N-[4-[2-(2-amino-4,7-dihydro-4-oxo-1Hpyrrolo[2,3-d] pyrimidin-5-yl)ethyl]benzoyl]-L-Glutamic acid (also known as pemetrexed diacid), having the following formula:

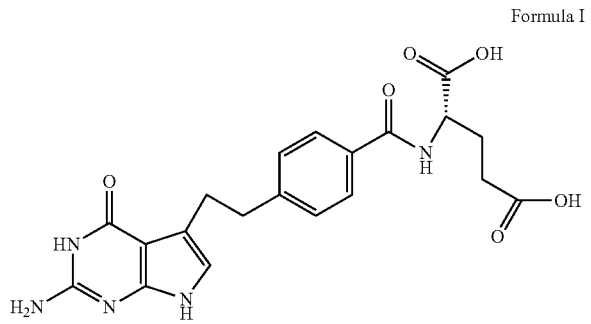 [SMILES: Nc1nc2[nH]cc(CCc3ccc(C(=O)N[C@@H](CCC(=O)O)C(=O)O)cc3)c2c(=O)[nH]1]

Formula I is a potent inhibitor of several folate-requiring enzymes and is useful for the treatment of non-small cell lung cancer and mesothelioma. Pemetrexed is available in market under the brand name ALIMTA® with the active ingredient chemically described as L-Glutamic acid, N-[4-[2-(2-amino-4,7-dihydro-4-oxo-1H-pyrrolo[2,3-d]pyrimidin-5-yl)ethyl]benzoyl]-disodium salt heptahydrate ("Pemetrexed disodium heptahydrate"). The commercially-available product, ALIMTA®, is supplied as a sterile lyophilized powder available in single-use vials for intravenous infusion.

Active pharmaceutical ingredients (APIs) can be prepared in a variety of different forms, such as, chemical derivatives, solvates, hydrates, co-crystals, or salts. APIs may also be prepared in different solid forms, in that they may be amorphous, may exist as different crystalline polymorphs, and/or in different salvation or hydration states. By varying the form of an API, it is possible to vary the physical properties thereof. For instance, solid forms of an API typically have different solubilities such that a more thermodynamically stable solid form is less soluble than a less thermodynamically stable solid form. Solid forms can also differ in properties such as shelf-life, bioavailability, morphology, vapor pressure, density, color, and compressibility. Accordingly, variation of the solid state of an API is one of many ways to modulate the physical and pharmacological properties thereof.

U.S. Pat. No. 5,344,932 ("the U.S. '932 patent"), which is incorporated herein by reference in its entirety, refers to pemetrexed diacid or a pharmaceutically acceptable salts thereof.

International application publication No. WO 01/14379 A2 ("the WO '379 publication") describes novel crystalline form of Pemetrexed disodium designated as "Hydrate Form I". According to WO '379 publication, the term "hydrate" describes crystalline lattice of pemetrexed disodium salt, which can contain variable amounts of water, from about 0.01 to about 3 equivalents of water, depending upon relative humidity in the storage conditions and preferably hydrate Form I contains from about 2 to about 3 equivalents of water, most preferred is 2.4-2.9 equivalents of water. Therefore, the "Hydrate form I" may not be suitable for making the finished dosage form of pemetrexed disodium because of the difficulties encountered due to its disadvantageous properties such as hygroscopic nature, and retaining variable amounts of water based on relative humidity.

U.S. Pat. No. 7,138,521 ("the U.S. '521 patent") describes that pemetrexed disodium can exist in another crystalline form i.e., a heptahydrate form which is more stable than the previously known 2.5 hydrate and the primary advantages of the heptahydrate crystalline form is stability with respect to the solvent content and stability with respect to growth of related substances. However, according to the U.S. '521 patent, the heptahydrate crystalline form when subjected to elevated temperatures, low humidity and/or vacuum, converts to the 2.5 hydrate crystal form by loss of water. In view of said limitations, the process for the preparation of heptahydrate requires specific critical conditions which are described in Column 3, lines 4-30 of the U.S. '521 patent and one of which is drying under humid nitrogen to remove the acetone content and maintain the desired water content. In view of the above, "heptahydrate crystalline form" may not be well suited for making the finished dosage form of pemetrexed disodium because of the difficulties encountered due to its disadvantageous properties such as polymorphic stability at low humidity and/or vacuum condition and converting to a lower hydrate by loss of water when exposed to elevated temperatures.

In order to overcome the difficulties connected with the hygroscopic nature and polymorphic stability of the known forms of pemetrexed disodium, some research groups focused on discovering new crystalline forms of pemetrexed disodium with better physical parameters.

International application publication No. WO 2011/064256 A1 ("the WO '256 publication") and Chinese Patent no. 1778802 ("the CN '802 patent") describe different crystalline form of pemetrexed disodium.

However, the diversity of crystalline forms of pemetrexed disodium may be disadvantageous to keep uniformity of different manufacturing batches and as a consequence to preserve uniformity in the finished dosage form.

In order to overcome the difficulties associated with reported polymorphic forms of pemetrexed disodium, some research groups focused on discovering new crystalline forms of pemetrexed diacid and novel polymorphs of other salts forms of pemetrexed.

International application publication No. WO 2008/021405 A1 ("the WO '405 publication") and WO2010/031357 A1 ("the WO '357 publication") describe various crystalline forms of pemetrexed diacid and process for their preparation.

It may be noted that, according to the description provided in the WO '379 publication, there are several disadvantages associated with pemetrexed diacid, for e.g., it is highly toxic requiring special handling measures and equipments and also isolation of the acid requires difficult operation which is time consuming and costly.

Chinese Patent Application No. CN 101033227, CN 10691371 and CN 1,552,713 disclose different new salts of pemetrexed and processes for preparation thereof. However, the polymorphic forms of these salts may not be useful due to their physico chemical properties such as lower solubility.

In order to overcome the disadvantages associated with the reported polymorphic forms of pemetrexed diacid, pemetrexed disodium and the other salts of pemetrexed, the inventors of the present application felt that there is a need to provide novel crystalline forms of pemetrexed tromethamine salts which have improved physical properties and deprived of the disadvantageous associated with known polymorphic forms of pemetrexed diacid, pemetrexed disodium and the other salts of pemetrexed.

The present invention relates to novel crystalline forms of pemetrexed tromethamine salts that are useful for manufacture of pharmaceutical dosage forms and possess one or more properties that provide advantages when used as an API. The present invention also provides processes for preparation of such novel crystalline forms.

SUMMARY OF THE INVENTION

An aspect of the present invention relates to pemetrexed tromethamine salts.

Another aspect of the present invention relates to crystalline pemetrexed tromethamine salt.

Further aspect of the present invention relates to crystalline forms of pemetrexed tromethamine salt.

An aspect of the present invention relates to a process for preparing pemetrexed tromethamine salt, said process comprises the steps of:
a) combining pemetrexed diacid and tromethamine in an organic solvent;
b) stirring the reaction mixture of step a) at a temperature of about 0° C. to about reflux temperature;
c) isolating the pemetrexed tromethamine salt; and
d) drying the product.

Another aspect of the present invention relates to a process for preparing pemetrexed tromethamine salt, said process comprises the steps of:
a) obtaining a solution of tromethamine in a $C_1$-$C_4$ alcohol solvent;
b) combining the solution of step a) with pemetrexed diacid;
c) maintaining the reaction mixture for a suitable time period; and
d) isolating the pemetrexed tromethamine salt.

In an another aspect the present invention relates to a process for preparing pemetrexed tromethamine salt, said process comprises the steps of:
a) preparing a solution of tromethamine in a polar solvent or mixture thereof
b) adding of pemetrexed diacid to the solution in step a)
c) adding of methyl ethyl ketone to the solution obtained
d) maintaining the reaction mixture for a suitable time period; and
e) isolating the pemetrexed tromethamine salt.

DETAILED DESCRIPTION

An aspect of the present invention relates to pemetrexed tromethamine salts.

In embodiments, the present invention relates solid state forms of pemetrexed tromethamine salt.

In embodiments, the present invention relates to crystalline pemetrexed tromethamine salt.

In embodiments, the present invention relates to crystalline forms of pemetrexed tromethamine salt.

In embodiments, the invention relates to a crystalline form of pemetrexed tromethamine salt that comprises at least one of Form 1, Form 2, Form 3, Form 4 and Form 5 of pemetrexed tromethamine salt.

Figure 2:
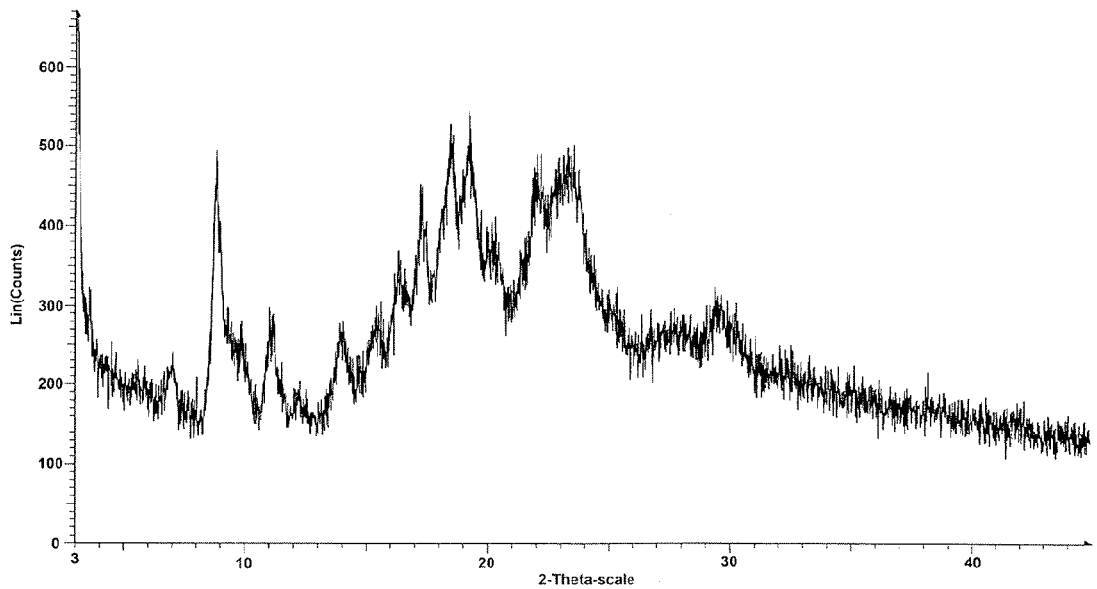
FIG. 2 is an illustration of a PXRD pattern of crystalline Form 1 of pemetrexed tromethamine (1:2) salt as obtained from example 1.

A crystalline Form 1 of pemetrexed tromethamine (1:2) salt as characterized by the PXRD of FIG. 2.

A crystalline Form 1 of pemetrexed tromethamine (1:2) salt as characterized by a PXRD pattern having peaks at about 6.9±0.2, 8.8±0.2, 9.8±0.2, 11.1±0.2, 13.9±0.2, 16.3±0.2, 17.25±0.2, 18.4±0.2, 19.2±0.2, 22.0±0.2, 23.7±0.2, and 29.4±0.2 (2θ degrees).

Figure 3:
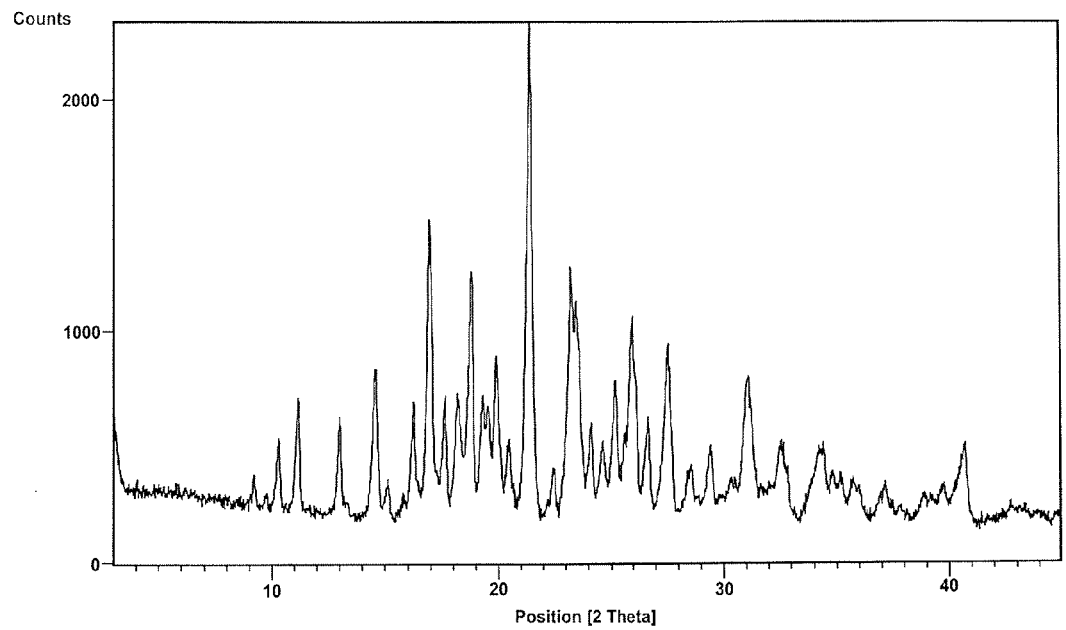
FIG. 3 is an illustration of a PXRD pattern of crystalline Form 2 of pemetrexed tromethamine (1:2) salt as obtained from example 4.

A crystalline Form 2 of pemetrexed tromethamine (1:2) salt as characterized by the PXRD of FIG. 3.

A crystalline Form 2 of pemetrexed tromethamine (1:2) salt as characterized by a PXRD pattern having peaks at about 9.1±0.2, 10.2±0.2, 11.1±0.2, 12.9±0.2, 14.5±0.2, 16.2±0.2, 16.9±0.2, 17.7±0.2, 18.7±0.2, 19.2±0.2, 19.6±0.2, 19.9±0.2, 20.4±0.2, 21.3±0.2, 23.1±0.2, 23.5±0.2, and 25.9±0.2 (2θ degrees).

Figure 4:
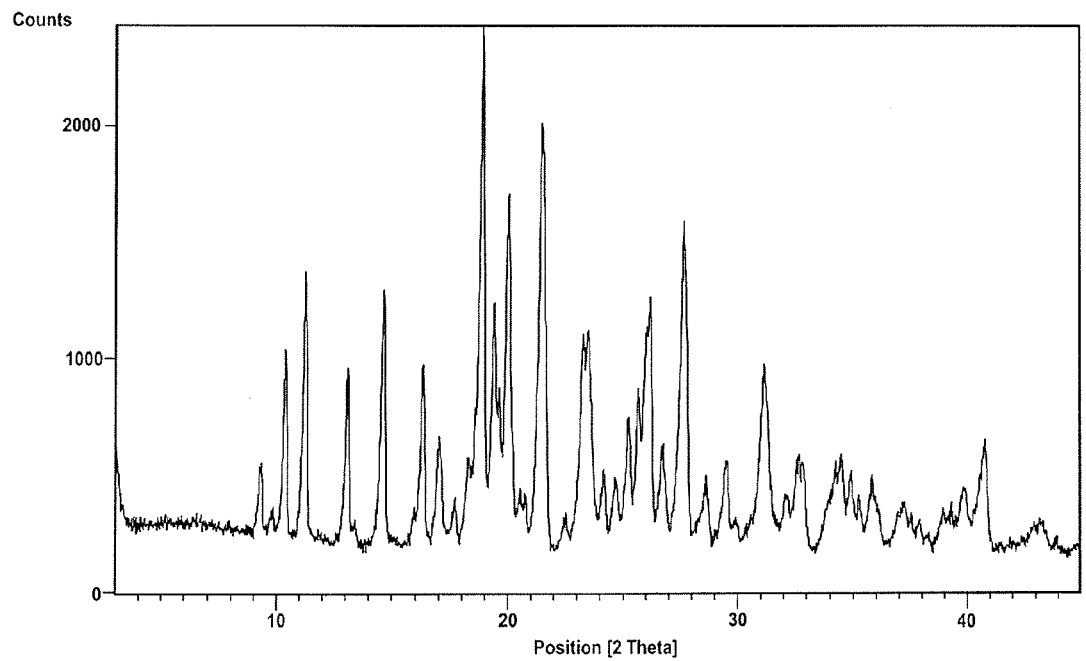
FIG. 4 is an illustration of a PXRD pattern of crystalline Form 3 of pemetrexed tromethamine (1:2) salt as obtained from example 5.

A crystalline Form 3 of pemetrexed tromethamine (1:2) salt as characterized by the PXRD of FIG. 4.

A crystalline Form 3 of pemetrexed tromethamine (1:2) salt as characterized by a PXRD pattern having peaks at about 9.3±0.2, 10.4±0.2, 11.2±0.2, 13.1±0.2, 14.6±0.2, 16.3±0.2, 17.0±0.2, 17.6±0.2, 18.2±0.2, 18.9±0.2, 19.4±0.2, 20.0±0.2, 21.5±0.2, 23.2±0.2, 23.5±0.2, 25.2±0.2, 25.6±0.2, 26.0±0.2, 26.2±0.2, 27.6±0.2, and 31.1±0.2 (2θ degrees).

Figure 5:
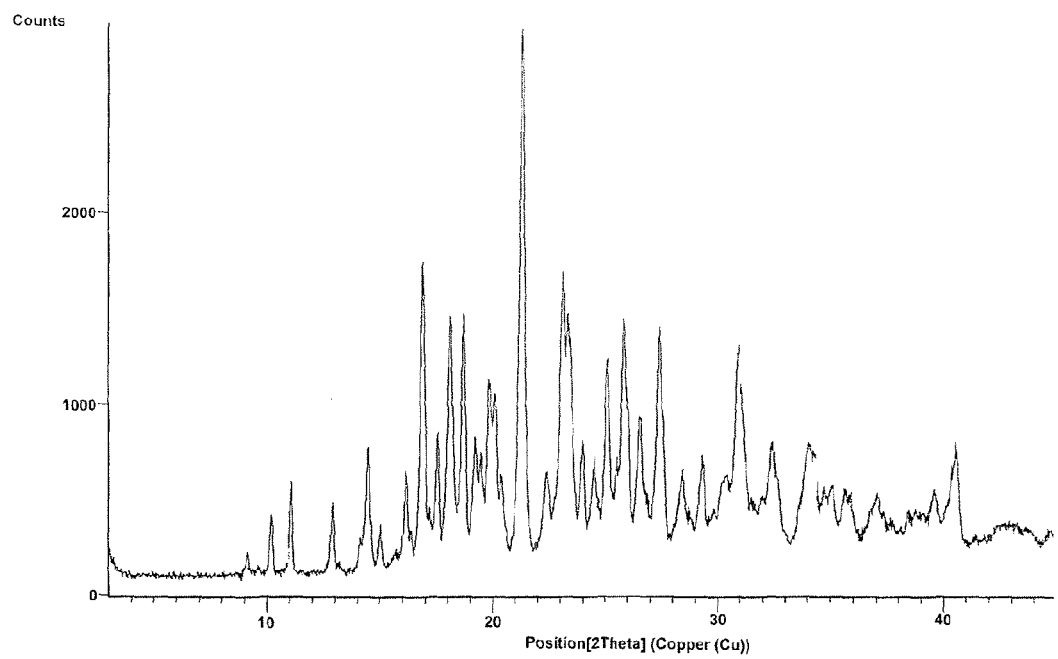
FIG. 5 is an illustration of a PXRD pattern of crystalline Form 4 of pemetrexed tromethamine (1:2) salt as obtained from example 6.

A crystalline Form 4 of pemetrexed tromethamine (1:2) salt as characterized by the PXRD of FIG. 5.

A crystalline Form 4 of pemetrexed tromethamine (1:2) salt as characterized by a PXRD pattern having peaks at about 4.9±0.2, 10.7±0.2, 11.3±0.2, 15.2±0.2, 15.8±0.2, 16.3±0.2, 16.8±0.2, 17.3±0.2, 19.0±0.2, 21.5±0.2, 22.5±0.2, 22.7±0.2, 23.9±0.2, 24.5±0.2, 25.8±0.2, 27.4±0.2, 28.5±0.2, 28.9±0.2, 29.9±0.2, and 31.6±0.2 (2θ degrees).

Figure 6:
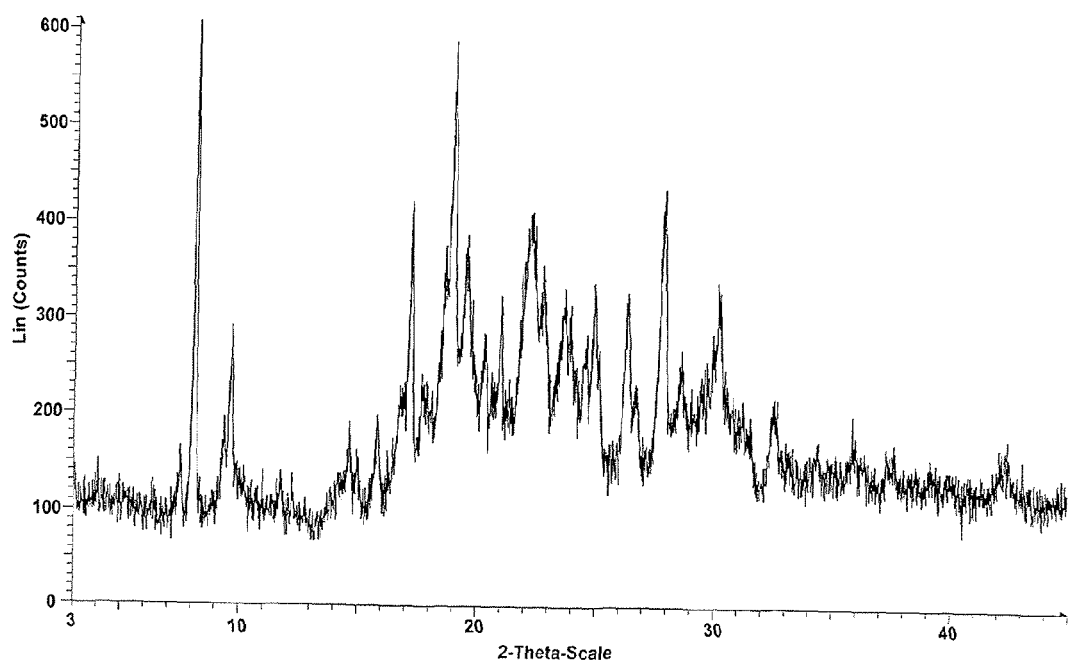
FIG. 6 is an illustration of a PXRD pattern of crystalline Form 5 of pemetrexed tromethamine (1:1) salt as obtained from example 7.

A crystalline Form 5 of pemetrexed tromethamine (1:1) salt as characterized by the PXRD of FIG. 6.

A crystalline Form 5 of pemetrexed tromethamine (1:1) salt as characterized by a PXRD pattern having peaks at about 9.3±0.2, 9.6±0.2, 14.6±0.2, 15.8±0.2, 16.7±0.2, 17.1±0.2, 17.6±0.2, 18.6±0.2, 18.9±0.2, 19.5±0.2, 20.2±0.2, 21.7±0.2, 22.2±0.2, 22.7±0.2, 23.6±0.2, 24.5±0.2, 24.9±0.2, 25.1±0.2, 26.3±0.2, 27.8±0.2, 28.5±0.2, 30.1±0.2, and 32.5±0.2 (2θ degrees).

The present application is also directed to processes for preparing pemetrexed tromethamine salts.

An aspect of the present application relates to a process for preparing pemetrexed tromethamine salt, said process comprises the steps of:
a) combining pemetrexed diacid and tromethamine in an organic solvent;
b) stirring the reaction mixture of step a) at a temperature of about 0° C. to about reflux temperature;
c) isolating the pemetrexed tromethamine salt; and
d) drying the product.

Step a) involves combining pemetrexed diacid and tromethamine in an organic solvent to obtain a reaction mixture.

The pemetrexed diacid may be obtained by known processes including the process disclosed by Charles et al. in Organic Process Research & Development 1999, 3, 184-188 or Edward et al. in *J. Med. Chem.* 1992, 35, 4450-4454 or the U.S. Pat. No. 5,344,932. Organic solvent used in step (a) may be selected from a group comprising aliphatic alcohols, such as methanol or ethanol; aliphatic ketones, such as acetone, methyl isobutyl ketone, methyl ethyl ketone; esters of carboxylic acids, such as ethyl acetate, isopropyl acetate; ethers, such as tetrahydrofuran; nitriles, such as acetonitrile, or their mixtures. In an embodiment, methanol, ethanol or acetone is used as the solvent.

Typical amounts of tromethamine that may be used can be varied based on the stoichiometric salt that is to be prepared, for example a pemetrexed tromethamine (1:1) salt or pemetrexed tromethamine (1:2) salt.

In an embodiment, 1 molar equivalent of tromethamine, per molar equivalent of pemetrexed diacid, is used. In another embodiment, 2 molar equivalents of teromethamine, per molar equivalent of pemetrexed diacid, is used.

The reaction mixture of pemetrexed diacid and tromethamine in an organic solvent is obtained by dissolving tromethamine in the organic solvent selected and combining the obtained solution with pemetrexed diacid. In an embodiment, the reaction mixture may be obtained at temperature ranging from about 0° C. to about reflux temperature of the solvent selected.

Step b) involves stirring the reaction mixture of step a) at a temperature of about 0° C. to about reflux temperature.

The reaction mixture of pemetrexed diacid and tromethamine in the organic solvent obtained in step a) is stirred and maintained at a temperature of about 0° C. to about reflux temperature of the solvent selected, to facilitate the formation of pemetrexed tromethamine salt.

In an embodiment, the reaction mixture of step a) is maintained at a temperature of about 10° C. to about 45° C., preferably at about 25° C. to about 35° C. The reaction mixture is maintained at the desired temperature for sufficient time to ensure the complete formation of pemetrexed tromethamine salt.

Step c) involves isolating the pemetrexed tromethamine salt. The pemetrexed tromethamine salt is isolated in a manner known per se, and depending on the solvent used, which include, but not limited to filtration by gravity or by suction, distillation, centrifugation, or slow evaporation or the like.

Step d) involves drying the product. The product obtained in step c) can be dried at a temperature less than about 50° C. to obtain pemetrexed tromethamine salt.

Another aspect of the present application relates to a process for preparing pemetrexed tromethamine salt, said process comprises the steps of:
a) obtaining a solution of tromethamine in a $C_1$-$C_4$ alcohol solvent;
b) combining the solution of step a) with pemetrexed diacid;
c) maintaining the reaction mixture for a suitable time period; and
d) isolating the pemetrexed tromethamine salt.

Step a) involves obtaining a solution of tromethamine in a $C_1$-$C_4$ alcohol solvent.

The solution of step a) may be obtained by dissolving tromethamine in a $C_1$-$C_4$ alcohol solvent. $C_1$-$C_4$ alcohol solvent used in step (a) may be selected from a group consisting of methanol, ethanol, isopropanol, n-propanol, n-butanol, 2-butanol or the like. Typical amounts of tromethamine that may be used can be varied based on the stoichiometric salt to be prepared, for example a pemetrexed tromethamine (1:1) salt or pemetrexed tromethamine (1:2) salt.

In an embodiment, 1 molar equivalent of tromethamine, per molar equivalent of pemetrexed diacid, is used to prepare a pemetrexed tromethamine (1:1) salt. In another embodiment, 2 molar equivalents of tromethamine, per molar equivalent of pemetrexed diacid is used to prepare a pemetrexed tromethamine (1:2) salt.

The solution of tromethamine may be obtained at a temperature of about 0° C. to about reflux temperature of the solvent selected, preferably at a temperature of about 40° C. to about 50° C.

Step b) involves combining the solution of step a) with pemetrexed diacid.

The pemetrexed diacid used in step a) may be obtained by known processes including the process disclosed by Charles et al. in Organic Process Research & Development 1999, 3, 184-188 or Edward et al. in *J. Med. Chem.* 1992, 35, 4450-4454 or the U.S. Pat. No. 5,344,932.

The solution of tromethamine in a $C_1$-$C_4$ alcohol solvent obtained in step a) is combined with pemetrexed diacid to obtain a reaction mixture of pemetrexed diacid and tromethamine. The solution of step a) may be combined with pemetrexed diacid at a temperature of about 0° C. to about reflux temperature of the solvent selected, preferably at a temperature of about 10° C. to about 45° C. more preferably at a temperature of about 25° C. to about 35° C.

Step c) involves maintaining the reaction mixture for a suitable time period.

The reaction mixture of pemetrexed diacid and tromethamine obtained in step b) is stirred and maintained for a suitable time period. Suitable time period according to the present application may be the time required to facilitate the formation of pemetrexed tromethamine salt. The reaction mixture may be maintained at a temperature of about 0° C. to about reflux temperature of the $C_1$-$C_4$ alcohol solvent selected to facilitate the formation of pemetrexed tromethamine salt. In an embodiment, the reaction mixture of step b) is maintained at a temperature of about 10° C. to about 45° C., preferably at about 25° C. to about 35° C. Step d) involves isolating the pemetrexed tromethamine salt. The pemetrexed tromethamine salt is isolated in a manner known per se, and depending on the solvent used, which include, but not limited to filtration by gravity or by suction, distillation, centrifugation, or slow evaporation or the like. The product obtained is dried at a temperature less than about 50° C. to obtain pemetrexed tromethamine salt.

In an another embodiment the present application relates to a process for preparing pemetrexed tromethamine salt, said process comprises the steps of:
   a) preparing a solution of tromethamine in a polar solvent or mixture thereof
   b) adding of pemetrexed diacid to the solution in step a)
   c) adding of anti solvent to the solution obtained
   d) maintaining the reaction mixture for a suitable time period; and
   e) isolating the pemetrexed tromethamine salt.

The pemetrexed diacid may be obtained by known processes including the process disclosed by Charles et al. in Organic Process Research & Development 1999, 3, 184-188 or Edward et al. in *J. Med. Chem.* 1992, 35, 4450-4454 or the U.S. Pat. No. 5,344,932.

Step a) preparing a solution of tromethamine in a polar solvent or mixture thereof Polar solvents used in step (a) may be selected from a group comprising water, aliphatic alcohols, such as methanol, ethanol, isopropanol, n-propanol, n-butanol, 2-butanol; aliphatic ketones, such as acetone, methyl isobutyl ketone, methyl ethyl ketone; esters of carboxylic acids, such as ethyl acetate, isopropyl acetate; ethers, such as tetrahydrofuran, 2-methyl THF, diethyl ether, di-isopropyl ether, methyl t-butyl ether; nitriles, such as acetonitrile, propionitrile or their mixtures. In an embodiment, methanol, isopropanol or water is used as the solvent.

Typical amounts of tromethamine that may be used can be varied based on the stoichiometric salt that is to be prepared, for example a pemetrexed tromethamine (1:1) salt or pemetrexed tromethamine (1:2) salt.

In an embodiment, 1 molar equivalent of tromethamine, per molar equivalent of pemetrexed diacid, is used. In another embodiment, 2 molar equivalents of tromethamine, per molar equivalent of pemetrexed diacid, is used.

The reaction mixture of tromethamine in a polar solvent is obtained by dissolving tromethamine in the polar solvent selected. In an embodiment, the reaction mixture may be obtained at temperature ranging from about 0° C. to about reflux temperature of the solvent selected, preferably at a temperature of about 20° C. to about 30° C.

Step b) adding of pemetrexed diacid to the solution in step a)

Pemetrexed diacid is added to the reaction mixture in lots or charged at once. In an embodiment the pemetrexed diacid may be added at temperatures ranging from about 0° C. to about reflux temperature preferably at a temperature of about 10° C. to about 30° C. In an embodiment, the reaction mixture may be maintained at temperatures ranging from about 0° C. to about reflux temperature of the solvent selected to obtain clear solution, preferably at a temperature of about 10° C. to about 30° C.

Step c) adding of anti solvent to the solution obtained

Anti solvent used in step c) may be selected from aliphatic ketones, such as acetone, methyl isobutyl ketone, methyl ethyl ketone; ethers, such as tetrahydrofuran, 2-methyl THF, diethyl ether, di-isopropyl ether; hydrocarbons like cyclohexane, n-hexane, n-heptane. In an embodiment, acetone, methyl isobutyl ketone, methyl ethyl ketone or mixtures thereof is used as the anti solvent. In an embodiment, anti solvent may be added at temperatures ranging from about −10° C. to about 50° C. based on the anti solvent selected, preferably at about 25° C. to about 30° C.

Step d) maintaining the reaction mixture for a suitable time period;

The reaction mixture of pemetrexed diacid and tromethamine obtained in step c) is stirred and maintained for a suitable time period. Suitable time period according to the present application may be the time required to facilitate the formation of pemetrexed tromethamine salt. The reaction mixture may be maintained at a temperature of about 0° C. to about reflux temperature of the anti solvent selected to facilitate the formation of pemetrexed tromethamine salt. In an embodiment, the reaction mixture of step d) is maintained at a temperature of about −10° C. to about 45° C., preferably at about 25° C. to about 35° C.

Step e) involves isolating the pemetrexed tromethamine salt.

The pemetrexed tromethamine salt is isolated in a manner known per se, and depending on the solvent used, which include, but not limited to filtration by gravity or by suction, distillation, centrifugation, or slow evaporation or the like. The product obtained is dried at a temperature less than about 50° C. to obtain pemetrexed tromethamine salt.

In an embodiment, the present application relates to a process for preparing pemetrexed tromethamine salt, said process comprises combining pemetrexed diacid with tromethamine.

In another embodiment, the present application relates to a process for preparing pemetrexed tromethamine salt, said process comprises the steps of:
   a) obtaining a solution of tromethamine in a $C_1$-$C_4$ alcohol solvent;
   b) combining the solution of step a) with pemetrexed diacid;
   c) isolating the pemetrexed tromethamine salt.

In an embodiment, the present application provides pemetrexed tromethamine (1:1) salt, which consists of one molecule of pemetrexed diacid and one molecule of tromethamine.

In another embodiment, the present application provides pemetrexed tromethamine (1:2) salt, which consists of one molecule of pemetrexed diacid and two molecule of tromethamine.

Figure 1:
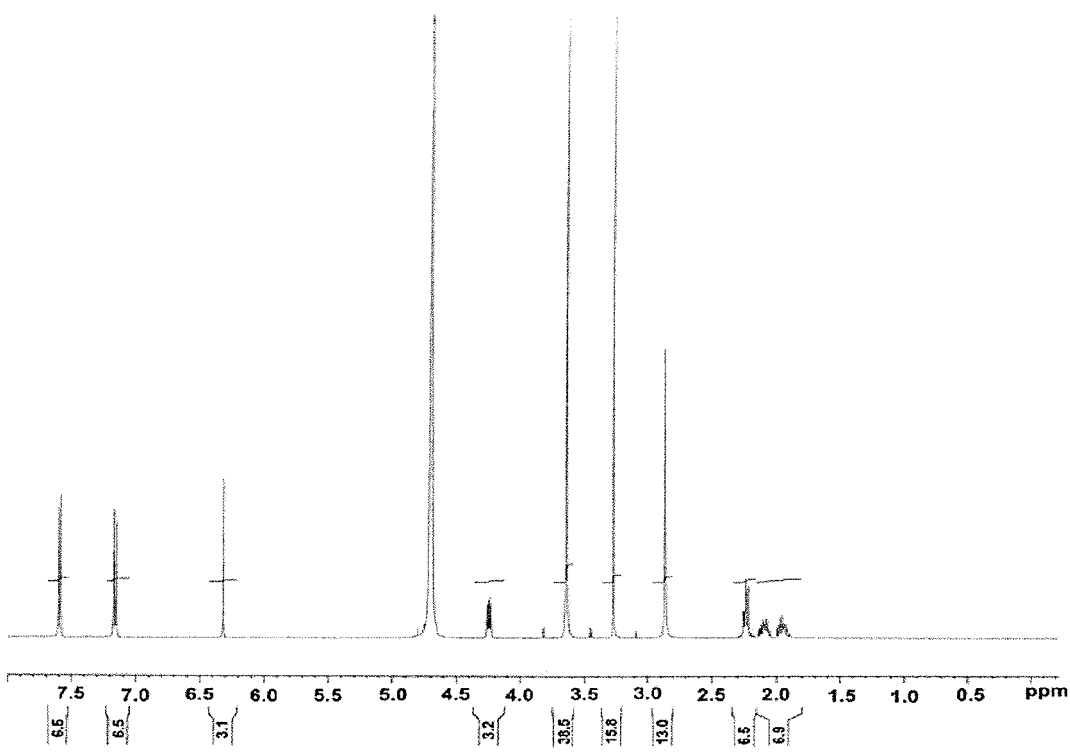
FIG. 1 shows a $^1$H-NMR spectra of pemetrexed tromethamine (1:2) salt.

In an embodiment, the present application provides pemetrexed tromethamine (1:2) salt, characterized by $^1$H-NMR spectra substantially as represented in FIG. 1.

In another embodiment, the present application provides pemetrexed tromethamine (1:2) salt, characterized by XRPD pattern substantially as represented in FIG. 2.

In an embodiment, the present application provides pemetrexed tromethamine (1:2) salt characterized by a powder XRD pattern substantially as represented in FIG. 3.

In an embodiment, the present application provides pemetrexed tromethamine (1:2) salt characterized by a powder XRD pattern substantially as represented in FIG. 4.

In an embodiment, the present application provides pemetrexed tromethamine (1:2) salt characterized by a powder XRD pattern substantially as represented in FIG. 5.

In an embodiment, the present application provides pemetrexed tromethamine (1:1) salt characterized by a powder XRD pattern substantially as represented in FIG. 5.

Figure 7:
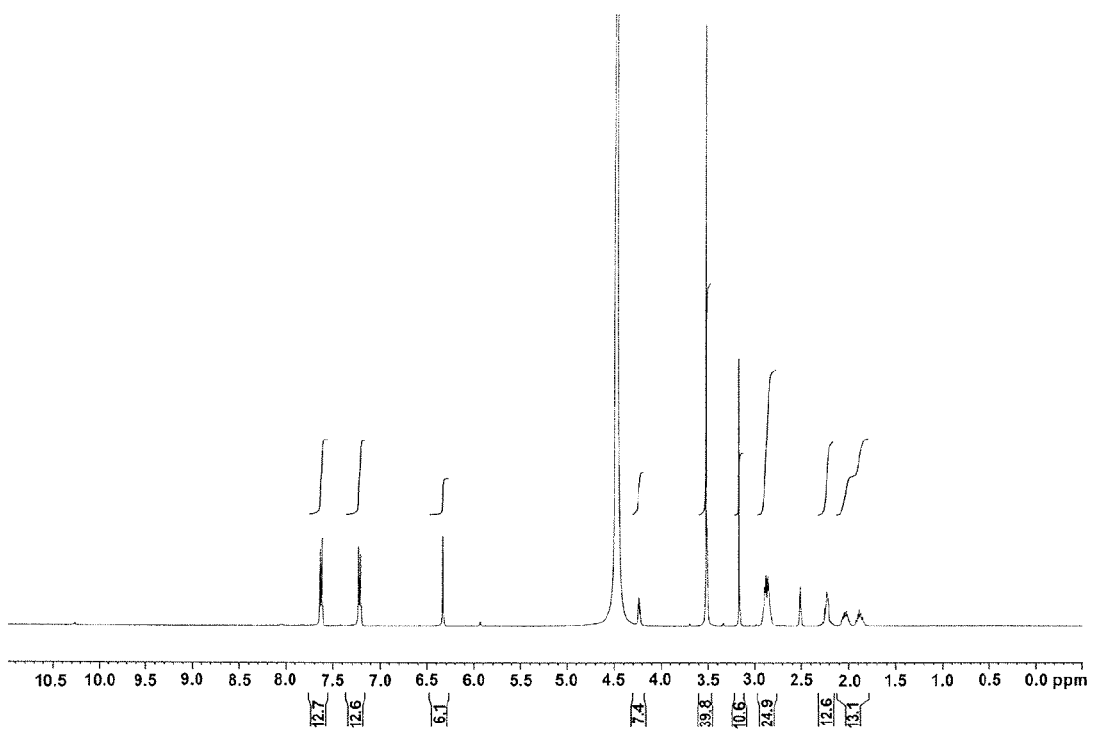
FIG. 7 shows a $^1$H-NMR spectra of pemetrexed tromethamine (1:1) salt.

In an embodiment, the present application provides pemetrexed tromethamine (1:1) salt, characterized by $^1$H-NMR spectra substantially as represented in FIG. 7.

The pemetrexed tromethamine salt and its novel crystalline forms of the present invention have advantageous properties selected from at least one: chemical purity, stability—such as storage stability, stability to dehydrate, stability to polymorphic conversion, flowability, solubility, morphology or crystal habit, low hygroscopicity and low content of residual solvents.

The crystalline pemetrexed tromethamine salts of the present invention are useful for the preparation of pharmaceutical formulations, preferably injectable formulations which are to be administered by intravenous, intramuscular, subcutaneous routes, intra-arterial or intrathecal route. More preferably, any of the novel crystalline form of pemetrexed tromethamine salts of the present invention is useful for the preparation of pharmaceutical formulations. Even more preferably, any of the novel crystalline form of pemetrexed tromethamine (1:2) salt of the present invention is useful for the preparation of pharmaceutical formulations.

As used herein, pharmaceutical formulation includes, but not limited to, lyophilized powder formulation, pre-lyophilization solution, liquid form ready for injection or infusion after reconstitution of a lyophilized preparation. Pharmaceutical formulation also includes liquid formulation, ready for injection or concentrate for further dilution before injection or infusion.

In one aspect, the input crystalline form is retained in finished formulation after lyophilization. In another aspect, the input crystalline form is converted to any of the novel crystalline form of pemetrexed tromethamine salt of this invention, in finished formulation after lyophilization. In another aspect, the input crystalline form is converted to any of the novel crystalline form of pemetrexed tromethamine salt of this invention or amorphous pemetrexed tromethamine salt or mixture thereof, in finished formulation after lyophilization.

The pharmaceutical formulations prepared using novel crystalline form of pemetrexed tromethamine of this invention, may additionally comprise at least one pharmaceutically acceptable excipient, for example, but not limited to, solvents, stabilizers, bulking agents, buffers, carriers, tonicity contributors, diluents, vehicles, solubilizers, pH adjusting agent or suitable mixtures thereof.

The pharmaceutically acceptable excipient includes, for example, but not limited to, mannitol, lactose, sucrose, maltose, dextrose, water, ethanol, propylene glycol, polyethylene glycols, glycerin, ascorbic acid and derivatives, cysteine, acetylcysteine, monothioglycerol, thioglycolic acid, lipoic acid, dihydrolipoic acid, methionine, butyl-hydroxyanisole, butyl-hydroxytoluene, tocopherol and derivatives, citric acid and derivatives, sodium formaldehyde sulfoxylate, sodium metabisulphite, EDTA and derivatives, acetate, glutamate, phosphate, benzoate, lactate, tartarate, sodium hydroxide, tromethamine and hydrochloric acid or mixture thereof.

The pharmaceutical formulation prepared using novel crystalline form of pemetrexed tromethamine salts of this invention, are useful for the treatment of various types of cancers in mammals.

Certain specific aspects and embodiments of the present application will be explained in more detail with reference to the following examples, which are provided only for purposes of illustration and should not be construed as limiting the scope of the present application in any manner.

DEFINITIONS

Tromethamine is the primary amine, tris-(hydroxymethyl)-aminomethane, also named 2-amino-2-(hydroxymethyl)-1,3-propanediol, and described in Merck Index, Tenth Edition page 1395.

The term "pemetrexed" refers to pemetrexed diacid and isomers, solvates, prodrugs, complexes and hydrates, anhydrous forms thereof, and any polymorphic or amorphous forms or combinations thereof.

The term "formulation" refers to preparing a drug, e.g., pemetrexed tromethamine, in a form suitable for administration to a patient, such as a human. Thus, a "formulation" can include pharmaceutically acceptable excipients.

The term "pharmaceutically acceptable" as used herein describes substances or components that do not cause unacceptable losses of pharmacological activity or unacceptable adverse side effects. Examples of pharmaceutically acceptable ingredients are those having monographs in *United States Pharmacopeia* (*USP* 29) *and National Formulary* (*NF* 24), United States Pharmacopeial Convention, Inc, Rockville, Md., 2005 ("USP/NF"), or a more recent edition, and the components listed in the continuously updated Inactive Ingredient Search online database of the FDA. Other useful components that are not described in the USP/NF, etc. may also be used.

EXAMPLES

The X-ray powder diffraction patterns described herein were generated using a Bruker AXS D8 Advance powder X-ray diffractometer and Panalytical Xpert pro, with a copper K-α radiation source (1.5418 A°). Generally, a diffraction angle (2θ) in powder X-ray diffractometry may have permissible variation in the range of ±0.2°.

The $^1$H-NMR spectra were recorded on a Bruker 400 MHz instrument. Chemical shifts are expressed in parts per million (ppm, δ units). Coupling constants are in units of hertz (Hz). Splitting patterns describe apparent multiplicities. $^1$H-NMR spectra may be used to quantify the molar ratios between pemetrexed and tromethamine in the pemetrexed tromethamine salt.

For example, a sample of Pemetrexed tromethamine salt obtained by the process of the present application may be dissolved in D$_2$O solvent, a $^1$H-NMR spectra on Bruker 400 MHz, may be recorded. 1. The proton Ha (as designated in Formula II)

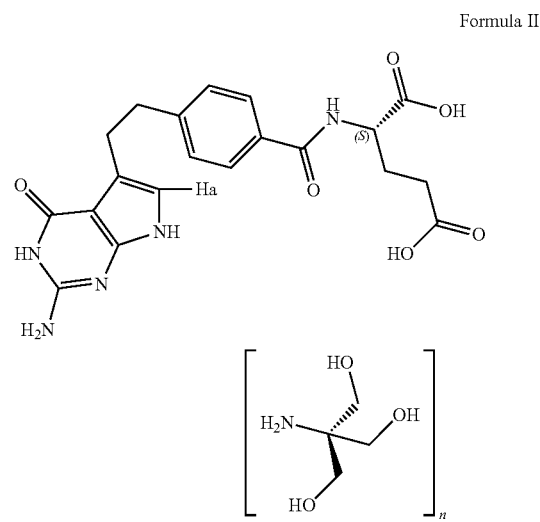

Formula II can be taken as the standard for estimating the number of protons in the pemetrexed tromethamine salt. For example, the ratio of the integral value of proton Ha and the integral value for the methylene protons of tromethamine provides the ratio between the pemetrexed and tromethamine in the pemetrexed tromethamine salt (e.g., n=1 or 2)

Example 1

Preparation of Pemetrexed Tromethamine (1:2) Salt (Formula II, n=2)

Tromethamine (1.7 g) and methanol (90 mL) are charged into a round bottom flask at 25-30° C., heated to a temperature of 40-50° C. and stirred for 10-15 minutes to obtain a clear solution. The reaction mixture is cooled to a temperature of 25-35° C., added pemetrexed diacid (3 g) and stirred at the same temperature for 1 hour. Methanol (30 mL) is added and the reaction mixture is stirred for 1 hour. The solid obtained is filtered, washed with methanol (30 mL), suction dried and dried under vacuum at 30° C. to give 4.05 g of title compound.

HPLC purity: 99.86%
$^1$H-NMR spectra: FIG. 1
XRPD pattern: FIG. 2.

Example 2

Preparation of Pemetrexed Tromethamine (1:2) Salt (Formula II, n=2)

To a solvent mixture of methanol (75 ml) and iso propyl alcohol (75 ml), 1.86 gms of Tromethamine was added at the room temperature and the temperature was raised to 56° C. and stirred till clear solution was obtained. To the clear reaction mass, charged pemetrexed diacid (3.0 gm) at 57° C. and stirred for about 24 hours. The reaction mass was then filtered and washed with methanol (15 ml), suction dried and dried under vacuum at 30° C. to yield 4.9 gms of the title compound.

HPLC purity: 99.87%
XRPD pattern: FIG. 2.

Example 3

Preparation of Pemetrexed Tromethamine (1:2) Salt (Formula II, n=2)

Methanol (250 ml) and Tromethamine (3.1 gm) were charged in a round bottom flask and stirred at room temperature for 10 minutes and charged pemetrexed diacid (5 gm). The reaction mass was stirred for 60 minutes and then distilled completely under vacuum. The solid thus obtained was dried under vacuum at 40° C. to yield 7.3 gms of the title compound HPLC purity: 99.66%
XRPD pattern: FIG. 2.

Example 4

Preparation of Pemetrexed Tromethamine (1:2) Salt (Formula II, n=2)

Tromethamine (3.1 gm) and water (10 ml) were charged in a round bottom flask at room temperature and stirred for 10 minutes. Pemetrexed diacid (5 gm) was added to the reaction mixture and stirred till a clear solution was obtained. To the obtained clear reaction mass added Methyl Ethyl Ketone (250 ml) and stirred for 2 hours. The separated solid was filtered and washed with Methyl Ethyl Ketone (25 ml) under vacuum. The wet solid was dried at 38° C. under vacuum in a rotavapour for 3 hours to obtain 6.35 gm of the Pemetrexed tromethamine (1:2) salt.

HPLC purity: 99.77%
XRPD pattern: FIG. 3.

Example 5

Preparation of Pemetrexed Tromethamine (1:2) Salt (Formula II, n=2)

Tromethamine (3.1 gm) and water (12.5 ml) were charged in a round bottom flask at room temperature and stirred for 10 minutes. Pemetrexed diacid (5 gm) was added to the reaction mixture at 15-20° C. and stirred till a clear solution was obtained. To the obtained clear reaction mass added Methyl Ethyl Ketone (175 ml) and acetone (20 ml) and stirred for 2 hours at room temperature. The separated solid was filtered and washed with Methyl Ethyl Ketone (25 ml) under vacuum. The wet solid was dried at 40° C. under vacuum in a rotavapour for 3 hours to obtain 6.34 gm of the Pemetrexed tromethamine (1:2) salt.

HPLC purity: 99.70%
XRPD pattern: FIG. 4.

Example 6

Preparation of Pemetrexed Tromethamine (1:2) Salt (Formula II, n=2)

Sodium hydroxide (3.82 gm) and water (30 ml) were charged in a round bottom flask under inert atmosphere and stirred for about 10 minutes. The temperature of the reaction mass was cooled to about 0-5° C. and then L-Glutamic acid, N-[4-[2-(2-amino-4,7-dihydro-4-oxo-1H-pyrrolo[2,3-d]pyrimidin-5-yl)ethyl] benzoyl]-,dimethyl ester 4-methylbenzene sulfonic acid salt (10 gm) was charged and stirred for one hour. $P^H$ of the reaction mass was adjusted to 5.4 with conc.HCl at 0-5° C. and stirred for 30 minutes at 25-30° C. Tromethamine (7.71 gm) was charged to the reaction mass and stirred for 30 minutes. To the reaction mass added Methyl Ethyl Ketone (350 ml) and acetone (50 ml) and stirred for 2 hours at 30-35° C. The separated solid was filtered and washed with Methyl Ethyl Ketone (50 ml) under vacuum. The wet solid was dried at 35-40° C. under vacuum for 3 hours to obtain 9.1 gm of the Pemetrexed tromethamine (1:2) salt.

HPLC purity: 98.05%
XRPD pattern: FIG. 5.

Example 7

Preparation of Pemetrexed Tromethamine (1:1) Salt (Formula II, n=1)

Tromethamine (0.85 g) and methanol (90 mL) are charged into a round bottom flask at 25-30° C., heated to a temperature of 40-50° C. and stirred for 10-15 minutes to obtain a clear solution. The reaction mixture is cooled to a temperature of 25-35° C., added pemetrexed diacid (3 g) and stirred at the same temperature for 2 hours. The solid obtained is filtered, washed with methanol (30 mL), suction dried and dried under vacuum at 30° C. to give title compound.

HPLC purity: 99.83%
XRPD pattern: FIG. 6.
$^1$H-NMR spectra: FIG. 7

The invention claimed is:
1. A crystalline pemetrexed tromethamine (1:2) salt.
2. The crystalline pemetrexed tromethamine (1:2) salt of claim 1 characterized by the PXRD as shown in FIG. 2.
3. The crystalline form according to claim 2 characterized by an X-ray Powder Diffraction Pattern having peaks at about 6.9±0.2, 8.8±0.2, 9.8±0.2, 11.1±0.2, 13.9±0.2, 16.3±0.2, 17.25±0.2, 18.4±0.2, 19.2±0.2, 22.0±0.2, 23.7±0.2, and 29.4±0.2(2θ degrees).
4. The crystalline pemetrexed tromethamine (1:2) salt of claim 1 characterized by the PXRD as shown in FIG. 3.
5. The crystalline form according to claim 4 characterized by an X-ray Powder Diffraction Pattern having peaks at about 9.1±0.2, 10.2±0.2, 11.1±0.2, 12.9±0.2, 14.5±0.2, 16.2±0.2, 16.9±0.2, 17.7±0.2, 18.7±0.2, 19.2±0.2, 19.6±0.2, 19.9±0.2, 20.4±0.2, 21.3±0.2, 23.1±0.2, 23.5±0.2, and 25.9±0.2(2θ degrees).
6. The crystalline pemetrexed tromethamine (1:2) salt of claim 1 characterized by the PXRD as shown in FIG. 4.
7. The crystalline form according to claim 6 characterized by an X-ray Powder Diffraction Pattern having peaks at about 9.3±0.2, 10.4±0.2, 11.2±0.2, 13.1±0.2, 14.6±0.2, 16.3±0.2, 17.0±0.2, 17.6±0.2, 18.2±0.2, 18.9±0.2, 19.4 ±0.2, 20.0±0.2, 21.5±0.2, 23.2±0.2, 23.5±0.2, 25.2±0.2, 25.6±0.2, 26.0±0.2, 26.2±0.2, 27.6±0.2, and 31.1±0.2(2θ degrees).
8. The crystalline pemetrexed tromethamine (1:2) salt of claim 1 characterized by the PXRD as shown in FIG. 5.
9. The crystalline form according to claim 8 characterized by an X-ray Powder Diffraction Pattern having peaks at about 4.9±0.2, 10.7±0.2, 11.3±0.2, 15.2±0.2, 15.8±0.2, 16.3±0.2, 16.8±0.2, 17.3±0.2, 19.0±0.2, 21.5±0.2, 22.5±0.2, 22.7±0.2, 23.9±0.2, 24.5±0.2, 25.8±0.2, 27.4±0.2, 28.5±0.2, 28.9±0.2, 29.9±0.2, and 31.6±0.2(2θ degrees).
10. A method for preparing a pharmaceutical composition comprising pemetrexed tromethamine, the method comprising combining the crystalline pemetrexed tromethamine (1:2) salt, of claim 1 and at least one pharmaceutically acceptable excipient.
11. A pharmaceutical formulation comprising crystalline pemetrexed tromethamine (1:2) salt of claim 1, and at least one pharmaceutically acceptable excipient.
12. A process for preparing the crystalline pemetrexed tromethamine (1:2) salt according to claim 1, comprising the steps of:
   a. combining pemetrexed diacid and tromethamine in an organic solvent;
   b. stirring the reaction mixture of step a) at a temperature of about 0° C. to about reflux temperature;
   c. isolating the pemetrexed tromethamine salt; and
   d. drying the product.
13. A process for preparing the crystalline pemetrexed tromethamine (1:2) salt according to claim 1, comprising the steps of:
   a. obtaining a solution of tromethamine in a $C_1$-$C_4$ alcohol solvent;
   b. combining the solution of step a) with pemetrexed diacid;
   c. maintaining the reaction mixture for a suitable time period; and
   d. isolating the pemetrexed tromethamine salt.
14. A process for preparing the crystalline pemetrexed tromethamine (1:2) salt according to claim 1, comprising the steps of:
   a. preparing a solution of tromethamine in a polar solvent or mixture thereof
   b. adding of pemetrexed diacid to the solution in step a)
   c. adding of anti-solvent to the solution obtained
   d. maintaining the reaction mixture for a suitable time period; and
   e. isolating the pemetrexed tromethamine salt.
15. A process for preparing the crystalline pemetrexed tromethamine (1:2) salt according to claim 1, comprising the steps of:
   a. obtaining a solution of tromethamine in a $C_1$-$C_4$ alcohol solvent;
   b. combining the solution of step a) with pemetrexed diacid;
   c. isolating the pemetrexed tromethamine salt.

* * * * *

UNITED STATES PATENT AND TRADEMARK OFFICE
CERTIFICATE OF CORRECTION

PATENT NO. : 9,688,682 B2
APPLICATION NO. : 14/905736
DATED : June 27, 2017
INVENTOR(S) : Ramesh Kumar Nadgoud et al.

It is certified that error appears in the above-identified patent and that said Letters Patent is hereby corrected as shown below:

Claim 10 should read as follows:

"A method for preparing a pharmaceutical composition, the method comprising combining the crystalline pemetrexed tromethamine (1:2) salt, of claim 1 and at least one pharmaceutically acceptable excipient."

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*